(12) United States Patent
Kron

(10) Patent No.: US 6,722,369 B1
(45) Date of Patent: Apr. 20, 2004

(54) TRACHEOSTOMY VENTILATOR TUBE HOLDER

(76) Inventor: Ronald C. Kron, 9111 Guttenberg Rd., Louisville, KY (US) 40291

( * ) Notice: Subject to any disclaimer, the term of this patent is extended or adjusted under 35 U.S.C. 154(b) by 0 days.

(21) Appl. No.: 10/262,505

(22) Filed: Oct. 1, 2002

(51) Int. Cl.[7] ............................................. A61M 16/00
(52) U.S. Cl. ........................... 128/207.17; 128/DIG. 26
(58) Field of Search ....................... 128/200.26, 207.14, 128/207.16, 207.17, 911, 912, DIG. 23, DIG. 26, DIG. 15; 604/174, 179; 2/137, 170

(56) References Cited

U.S. PATENT DOCUMENTS

| | | | |
|---|---|---|---|
| 3,927,676 A | * 12/1975 | Schultz | 128/207.17 |
| 4,313,437 A | 2/1982 | Martin | |
| 4,326,515 A | * 4/1982 | Shaffer et al. | 128/207.17 |
| 4,331,144 A | 5/1982 | Wapner | |
| 4,378,012 A | * 3/1983 | Brown | 128/207.17 |
| 4,449,527 A | * 5/1984 | Hinton | 128/207.17 |
| 4,622,034 A | * 11/1986 | Shattuck | 604/179 |
| 5,101,822 A | * 4/1992 | Kimmel | 128/207.14 |
| 5,237,988 A | * 8/1993 | McNeese | 128/207.17 |
| 5,271,745 A | * 12/1993 | Fentress et al. | 604/179 |
| 5,357,952 A | * 10/1994 | Schuster et al. | 128/207.17 |
| 5,471,980 A | * 12/1995 | Varner | 128/207.17 |
| 5,501,216 A | 3/1996 | Byrd | |
| 5,546,938 A | * 8/1996 | McKenzie | 128/207.17 |
| 5,671,732 A | 9/1997 | Bowen | |
| 5,782,236 A | 7/1998 | Ess | |
| 5,918,599 A | * 7/1999 | Shesol | 128/207.17 |
| 5,924,421 A | * 7/1999 | Rosbrook et al. | 128/207.14 |
| 6,009,872 A | 1/2000 | Delaplane et al. | |
| 6,047,699 A | 4/2000 | Ryatt et al. | |
| 6,105,573 A | 8/2000 | Delaplane et al. | |
| 6,105,577 A | 8/2000 | Varner | |
| 6,186,139 B1 | 2/2001 | Bezicot et al. | |
| 6,336,457 B1 | * 1/2002 | Hudson et al. | 128/207.17 |
| 6,412,117 B1 | * 7/2002 | Holmes et al. | 2/137 |

OTHER PUBLICATIONS

Product Brochure No. PS 240 by Dale Medical Products, Inc., having an address at 7 Cross Street, P.O. Box 1556, Plainville, MA 02762 ("Dale Tracheostomy Tube Holder").

* cited by examiner

Primary Examiner—Aaron J. Lewis
Assistant Examiner—Teena Mitchell
(74) Attorney, Agent, or Firm—David W. Carrithers; Carrithers Law Office, PLLC

(57) ABSTRACT

A holder for tracheostomy systems on a patient that can function as a tracheostomy tube holder or as a ventilator tube holder. The holder is a bifurcated strip of flexible material providing a principal portion and a pair of minor portions extending therefrom. The principal portion has a hole therethrough. The strip has portions of a hook and loop fastener adjacent respective opposite ends thereof.

13 Claims, 2 Drawing Sheets

TRACHEOSTOMY VENTILATOR TUBE HOLDER

BACKGROUND OF THE INVENTION

TECHNICAL FIELD

The present invention relates to an improved ventilator tube holder and more particularly to a holder comprising a strip of flexible material with a hole there through and beyond the hole the strip is bifurcated providing a pair of strips for passing respectively on opposite sides of a ventilator tube, or component of a ventilator system, connected to a tracheostomy tube. Opposite ends of the strip have cooperating portions of a hook and loop fastening means thereon that cooperate with one another for detachable interconnection or detachable interconnection with appropriate portions of corresponding fastening means on a tracheostomy tube holder that goes around the neck of a patient.

BACKGROUND OF THE INVENTION

Tracheostomy patients are fitted with a tracheostomy tube that has a flange, also referred to as a neck plate, intermediate the ends thereof. The plate limits the depth of penetration of one end portion of the tube through a hole in the patients neck into the trachea and an opposite end portion of the tube projects outwardly from the plate. The plate connects to the tube preferably in such a manner as to allow limited movement of the tube relative to the plate, e.g. a pivotal connection. A ventilator tube, or ventilator circuit component, connects to the opposite end portion of the tube that projects outwardly from the patients neck. Straps referred to as holders are used to retain the tracheostomy tube on the patients neck. Furthermore, straps are used to keep the ventilator tube, or ventilator circuit component as the case maybe, connected to the tube projecting from the patients neck. There are a variety of known devices serving these purposes as exemplified by the following United States Patents: U.S. Pat. No. 6,105,577 granted Aug. 22, 2000 to Scott H Varner; U.S. Pat. No. 6,105,373 granted Aug. 22, 2000 to David Delaplane et al; U.S. Pat. No. 6,047,699 granted Apr. 11, 2000 to Sadi Ryatt et al; U.S. Pat. No. 6,008,872 granted Jan. 4, 2000 to David Delaplane et al; U.S. Pat. No. 5,782,236 granted Jul. 21, 1998 to Steven M Ess; U.S. Pat. No. 5,671,732 granted Sep. 30, 1997 to Michael I Bowen; U.S. Pat. No. 5,501,216 granted Mar. 26, 1996 to Timothy N Byrd; U.S. Pat. No. 5,237,988 granted Aug. 24, 1993 to Wesley G McNeese; U.S. Pat. No. 4,331,144 granted May 25, 1982 to Herbert H Wapner; and U.S. Pat. No. 4,313,437 granted Feb. 2, 1982 to Dianne I Martin.

The forgoing patents disclose various strap means that loop through a spaced apart pair of slots in a neck plate having a tube attached thereto that projects though a hole in a patients neck into the trachea. The straps go around the patients neck and thereby hold the tube device in position. The '699 patent and the '236 patent additionally have means for ensuring a ventilator tube remains attached to the patient mounted device. In all instances the holder for the patient mounted device and the holder for the ventilator tube are completely unrelated and thus bear no similarity to one another. There is absolutely no way one of the known holders for one purpose could be substituted for one of the known holders serving the other of the two purposes.

SUMMARY OF INVENTION

The present invention provides a holder for use on tracheostomy patients comprising a flexible strip of material having a principal strip portion with a hole there through and a bifurcated portion that provides two minor strip portions extending from said principal strip portion. One such holder maybe used to retain the tracheostomy tube on the patient and another such holder used to ensure the ventilator tube (or ventilator system component) remains connected to the patient attached device.

BRIEF DESCRIPTION OF THE DRAWINGS

A better understanding of the present invention will be had upon reference to the following description in conjunction with the accompanying drawings in which like numerals refer to like parts throughout the several views and wherein.

DESCRIPTION OF THE PREFERRED EMBODIMENTS

Figure 1:
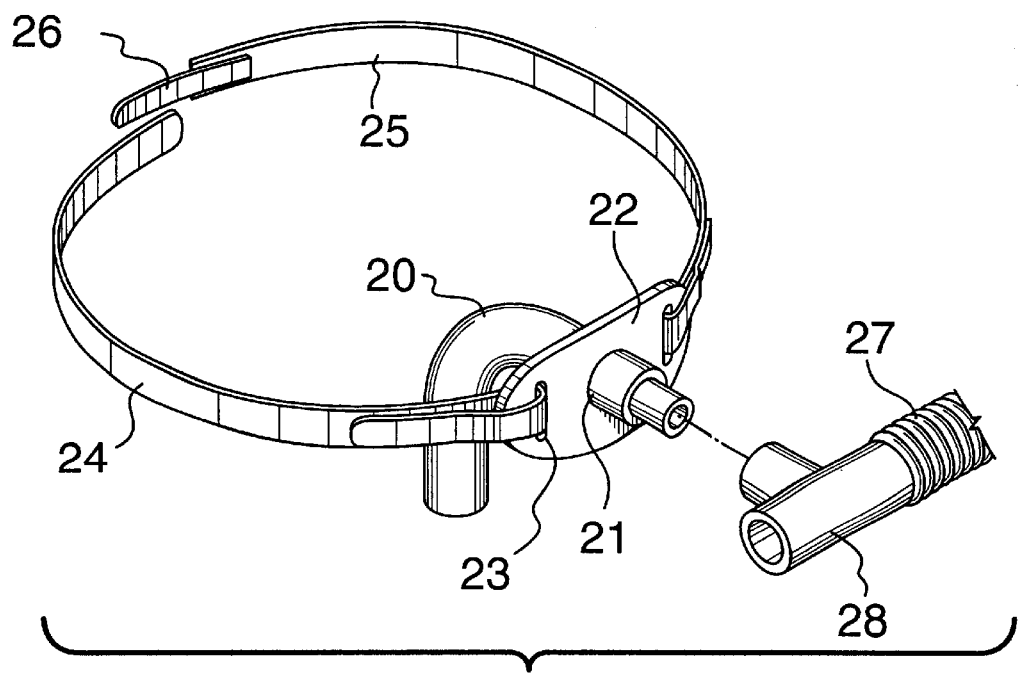
FIG. 1 is an exploded oblique view of a prior art tracheostomy tube having a strap attached thereto for retaining the same on a patient and a portion of a ventilator tube attached to a connector of a ventilator system.

Referring to FIG. 1, there is illustrated a prior art tracheostomy tube 20 pivotally connected as at 21 to a throat plate 22. The throat plate has a pair of elongate slots 23 and connected to the same is one end of respective straps 24, 25. The other end of the straps have cooperating portions of a hook and loop fastener 26 for detachably interconnecting the free ends of the straps. The straps 24, 25 constitute a tracheostomy tube holder.

A portion of a ventilator system is shown comprising a ventilator tube 27 that is connected to a connector 28 having a portion thereof that slip fits onto a portion of the tracheostomy tube 20 (and/or an inner tube that slides into the tube 20) that projects from the throat plate. In practice, a holder is used to ensure that the ventilator system remains attached to the tracheostomy tube and a holder for that purpose is disclosed in the above mentioned U.S. Pat. No. 6,047,699. Another holder serving the same purpose is disclosed in the above mentioned U.S. Pat. No. 5,782,236. Each of these known ventilator tube holders are connected to the throat plate of the tracheostomy tube.

Figure 2:
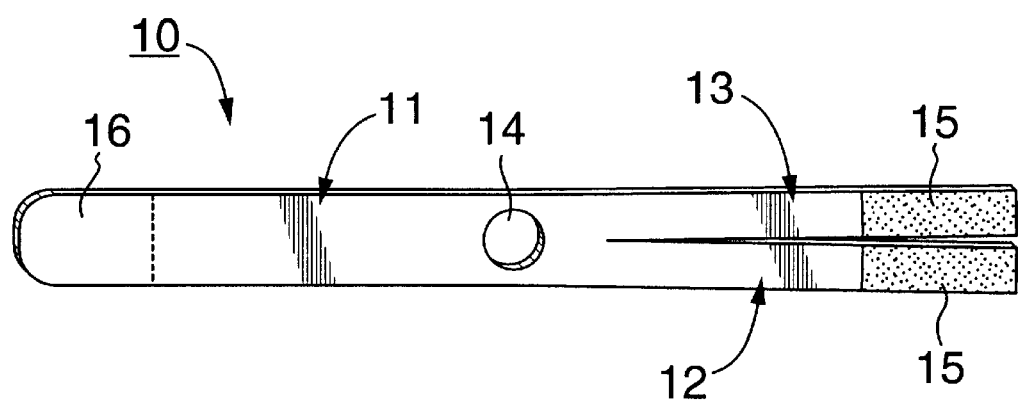
FIG. 2 is an oblique view of a holder provided in accordance with the present invention for use with the apparatus shown in FIG. 1 or the equivalent thereof for used for the same purpose.

A holder 10, provided in accordance with the present invention, is illustrated in FIG. 2, and comprises a strip of flexible material that has a principal portion 11 with a hole 14 there through and a bifurcated portion providing two side-by-side minor portions 12 and 13 extending from the principal portion. The strip generally is referred to herein as a bifurcated strip. Opposite ends of the strip have thereon portions of a hook and loop fastening means for detachable interconnection or detachable connection with similar fastening means portions on a tracheostomy tube holder.

The strip is made of a soft material for patient comfort or has portions of soft material attached thereto at suitable locations to provide the required comfort. Also, the strip, or portions thereof, maybe made of an elastic or elasticized or stretch material so as to provide a snug fit around a patients neck and also allow for muscle reflex due to coughing.

The terminal ends of the strip have cooperating portions of a hook and loop fastener for connecting the ends to one another or to another holder around the patients neck that is used to retain the tracheostomy tube on the patient. The strip portions 12, 13 each have, for example as illustrated in the drawings, a piece 15 secured thereto which is one portion of a hook and loop fastener and the terminal end of the principal portion 11 has a piece 16 thereon of the other cooperating portion of the hook and loop fastener. These are of suitable length and appropriately located so as to accommodate different neck sizes. One well known hook and loop fastener is sold under the Trademark VELCRO which is familiar to everyone and thus is not described further. Of course it is contemplated that a series of metal or plastic hooks and loops, or buttons and holes, or snaps, or other means for fastening could be used to hold and connect the distal ends of the strips together to secure the holder around the patient's neck.

Figure 3:
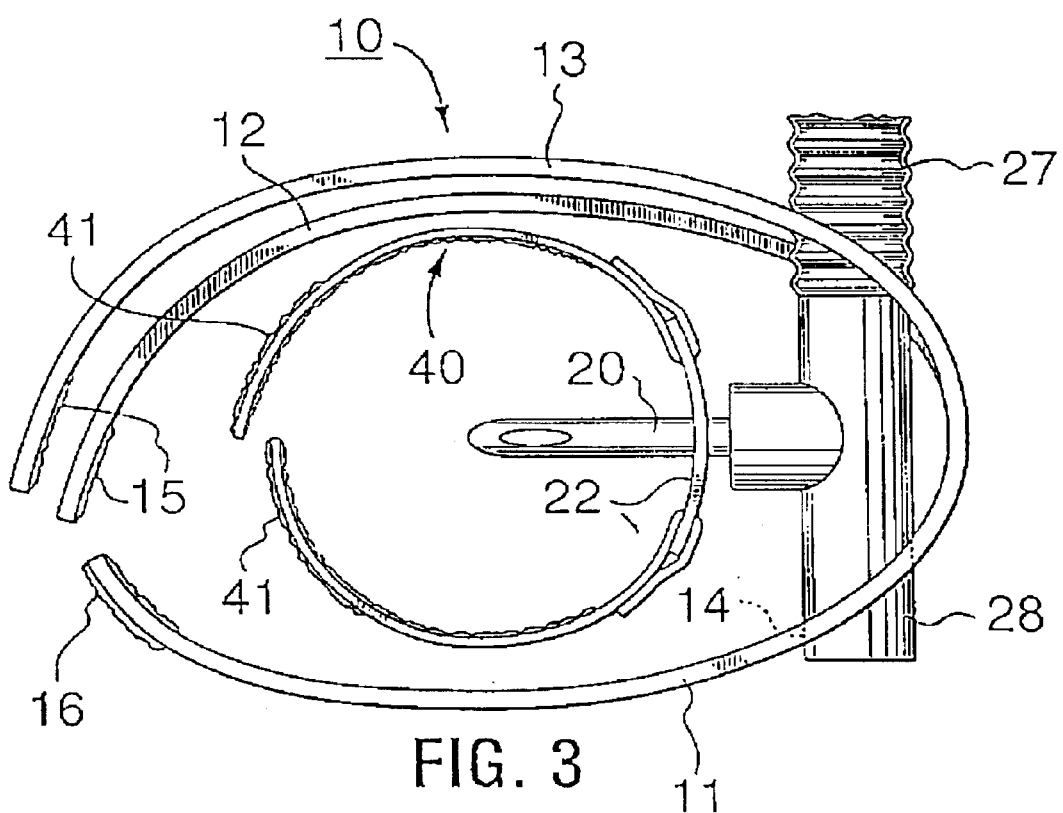
FIG. 3 is a plan view showing the device of FIG. 2 used in accordance with one aspect of the present invention to ensure that the ventilating tube remains connected to the patient mounted tracheostomy tube.

The forgoing strip 10, while primarily intended and designed as a simple device to ensure a ventilator tube, or component of a ventilator system as the case maybe, remains attached to a patient mounted tracheostomy tube and which use is illustrated by way of example in FIG. 3. It can also be used as a tracheostomy tube holder and such use is illustrated by way of example in FIG. 4.

Referring to FIG. 3, the ventilator system connector 28 is shown connected to an outer end of the tracheostomy tube 20. A holder 10, of the present invention shown in FIG. 2, has a portion of the connector 28 projecting through the hole 14. The ventilator tube 27 passes between the strip portions 12, 13 with one such strip being above the tube and the other below the tube. The strip goes around the patients neck (not shown) and the terminal ends are readily detachably interconnected by the cooperating hook and loop fastener portions 15, 16 or detachably connected to the outer face of a tracheostomy tube holder 40, in which case the outer face of the tracheostomy tube holder is provided with suitable portions of a hook and loop type fastener and located at suitable locations. The tracheostomy tube holder 40 maybe a known prior art type illustrated by way of example in FIG. 1 and provided with appropriate portions of a hook and loop fastening means 41 at suitable locations on the outer surface thereof or alternatively the holder 40 maybe a second holder 10 serving a tracheostomy tube holder.

Figure 4:
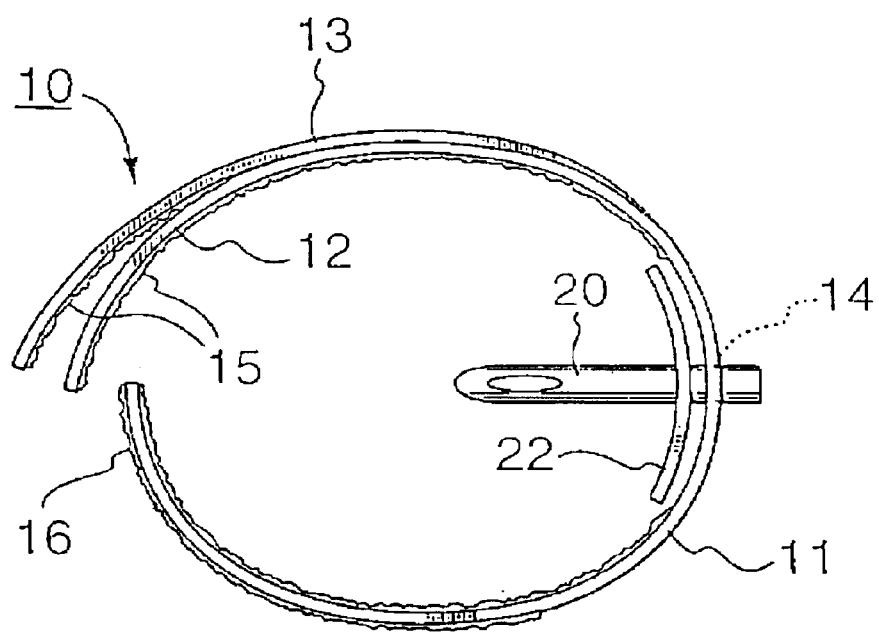
FIG. 4 is a plan view of the strip of FIG. 2 used in accordance with another aspect of the present invention to retain the tracheostomy tube on the patient.

Referring to FIG. 4 there is illustrated a holder 10 of the present invention serving as a tracheostomy tube holder and wherein the strip portion 11 overlies the throat plate 22 and the tracheostomy tube 20 projects through the hole 14. The strip 10 encircles the patients neck and the cooperating hook and loop strip connector portions detachably join the ends of the two minor strip portions 12, 13 to the principal strip portion 11. The fastener portions can be suitably positioned so that the strip can be adjusted to fit comfortably around various neck sizes.

The foregoing detailed description is given primarily for clearness of understanding and no unnecessary limitations are to be understood therefrom, for modifications will become obvious to those skilled in the art based upon more recent disclosures and may be made without departing from the spirit of the invention and scope of the appended claims.

I claim:

1. A holder for use on tracheostomy patients, comprising:
   a tracheostomy tube holder;
   a ventilator tube in flow communication with a tracheostomy tube extending through said tracheostomy tube holder;
   a bifurcated strip of flexible material, said strip having a principal strip portion with a hole therein for inserting said tracheostomy tube and a pair of minor distal end strip portions extending from said principal strip portion;
   said principal strip having a distal end including a first means for fastening; and
   each one of said minor strip portions having a distal end including a second means for fastening for cooperatively engaging said first means for fastening of said distal end of said principal strip.

2. The holder as defined in claim 1, wherein at least a selected length portion of said strip of material is stretchable.

3. The holder as defined in claim 2, wherein at least a selected portion of said strip of material has a soft outer surface.

4. The holder as defined in claim 1, wherein said means for fastening comprises hook and loop fasteners.

5. The holder as defined in claim 1, wherein said means for fastening comprises buttons and holes or snaps.

6. The holder as defined in claim 1, wherein said tracheostomy tube holder includes means for fastening at a selected location on an outer surface thereof for cooperatively engaging said means for fastening to said distal end of said principal strip or at least one of said minor distal end strip portions.

7. A tracheostomy ventilator tube holder for use on tracheostomy patients, comprising:
   a tracheostomy tube holder;
   a ventilator tube component in flow communication with a tracheostomy tube extending through said tracheostomy tube holder;
   a bifurcated strip of flexible material, said strip having a principal strip portion with a hole therein for inserting said tracheostomy tube and a pair of minor distal end strip portions extending from said principal strip portion;
   said principal strip having a first distal end including means for fastening;
   each one of said minor strip portions having a second distal end including attachment means for cooperatively engaging said means for fastening of said first distal end of said principal strip;
   whereby wrapping said bifurcated strip of flexible material around a patient's neck with said pair of minor distal end portions extending around at least a portion of said ventilator tube component disposed therebetween and connecting said means for fastening of said pair of minor distal end portions to said means of fastening of said first distal end of said principal strip holds said ventilator tube component in position with respect to said tracheostomy tube and said patient's neck, and upon removal of said ventilator component said tracheostomy tube can be inserted through said hole in said principal strip and connecting said means for fastening of said pair of minor distal end portions to said means of fastening of said first distal end of said principal strip holds said tracheostomy tube in position with respect to said patient's neck.

8. The holder as defined in claim 7, wherein at least selected length portions of said strip of material is stretchable.

9. A holder as defined in claim 8, wherein at least selected portions of said strip of material has a soft outer surface.

10. The holder as defined in claim 7, wherein at least a selected length portion of said strip of material is stretchable.

11. The holder as defined in claim 7, wherein at least a selected portion of said strip of material has a soft outer surface.

12. The holder as defined in claim 7, wherein said means for fastening comprises hook and loop fasteners.

13. The holder as defined in claim 7, wherein said means for fastening comprises buttons and holes or snaps.

* * * * *